United States Patent
Schmidt et al.

(10) Patent No.: US 10,033,068 B2
(45) Date of Patent: Jul. 24, 2018

(54) COMPOSITION INCLUDING A PENTACYCLIC ANION SALT AND USE THEREOF AS A BATTERY ELECTROLYTE

(71) Applicant: ARKEMA FRANCE, Colombes (FR)

(72) Inventors: Grégory Schmidt, Saint Andeol le Chateau (FR); Bruno Van Hemelryck, Chaponost (FR)

(73) Assignee: ARKEMA FRANCE, Colombes (FR)

( * ) Notice: Subject to any disclaimer, the term of this patent is extended or adjusted under 35 U.S.C. 154(b) by 64 days.

(21) Appl. No.: 15/026,806

(22) PCT Filed: Sep. 22, 2014

(86) PCT No.: PCT/FR2014/052348
§ 371 (c)(1),
(2) Date: Aug. 1, 2016

(87) PCT Pub. No.: WO2015/049435
PCT Pub. Date: Apr. 9, 2015

(65) Prior Publication Data
US 2017/0040640 A1     Feb. 9, 2017

(30) Foreign Application Priority Data

Oct. 3, 2013 (FR) ..................... 13 59602

(51) Int. Cl.
*H01M 10/0568* (2010.01)
*C07D 233/90* (2006.01)
(Continued)

(52) U.S. Cl.
CPC ...... *H01M 10/0568* (2013.01); *C07D 233/90* (2013.01); *H01M 10/0525* (2013.01); *H01M 10/052* (2013.01); *H01M 2300/0025* (2013.01)

(58) Field of Classification Search
CPC ......... H01M 10/0568; H01M 10/0525; H01M 2300/0025; H01M 10/052; C07D 233/90
See application file for complete search history.

(56) References Cited

U.S. PATENT DOCUMENTS

| | | | |
|---|---|---|---|
| 2002/0102380 A1* | 8/2002 | Michot | ................ B01J 31/0215 428/64.8 |
| 2005/0123831 A1* | 6/2005 | Michot | ................ B01J 31/0215 429/188 |

(Continued)

FOREIGN PATENT DOCUMENTS

| WO | WO 2010/023413 A1 | 3/2010 |
|---|---|---|
| WO | WO 2013/072591 A1 | 5/2013 |

OTHER PUBLICATIONS

M. Bukowska et al, "Synthesis of 4,5-Dicyanoimidazoles", Polish J. Chem., 78, 417-422 (2004) 6 pages.

(Continued)

*Primary Examiner* — Stewart A Fraser
(74) *Attorney, Agent, or Firm* — Buchanan Ingersoll & Rooney P.C.

(57) ABSTRACT

A composition including: (i) a lithium salt of imidazole compound of formula (I): wherein Rf is a fluorinated alkyl group having 1 to 5 carbon atoms, or a fluorine atom; and (ii) at least one cation selected from the group A including sodium, potassium, calcium, iron, magnesium, manganese, strontium, vanadium, ammonium, silver, aluminium, arsenic, barium, silicon, cadmium, cobalt, chromium, copper, nickel, lead, antimony, selenium, tin, strontium and titanium; and (iii) at least one anion chosen from the group B including fluoride, chloride, nitrate, sulphate, phosphate, trifluoroacetate, pentafluoroacetate and the anion of formula (II), with all the cation(s) and anion(s) being more than 0 wt % and at most 1 wt % of the composition. Also, the (Continued)

x : Wavenumber in cm-1 preparation of the composition as well as to the use of the composition as a battery electrolyte.

16 Claims, 1 Drawing Sheet

(51) Int. Cl.
*H01M 10/0525* (2010.01)
*H01M 10/052* (2010.01)

(56) References Cited

U.S. PATENT DOCUMENTS

2011/0311884 A1   12/2011   Armand et al.
2014/0315079 A1   10/2014   Schmidt et al.

OTHER PUBLICATIONS

L. Niedzicki et al, "New Type of Imidazole Based Salts Designed Specifically for Lithium Ion Batteries," Electrochimica Acta 55, 1450-1454 (2010) 6 pages.
International Search Report (PCT/ISA/210) dated Nov. 25, 2014, by the Japanese Patent Office as the International Searching Authority for International Application No. PCT/FR2014/052348.
Written Opinion (PCT/ISA/237) dated Nov. 25, 2014, by the Japanese Patent Office as the International Searching Authority for International Application No. PCT/FR2014/052348.

* cited by examiner

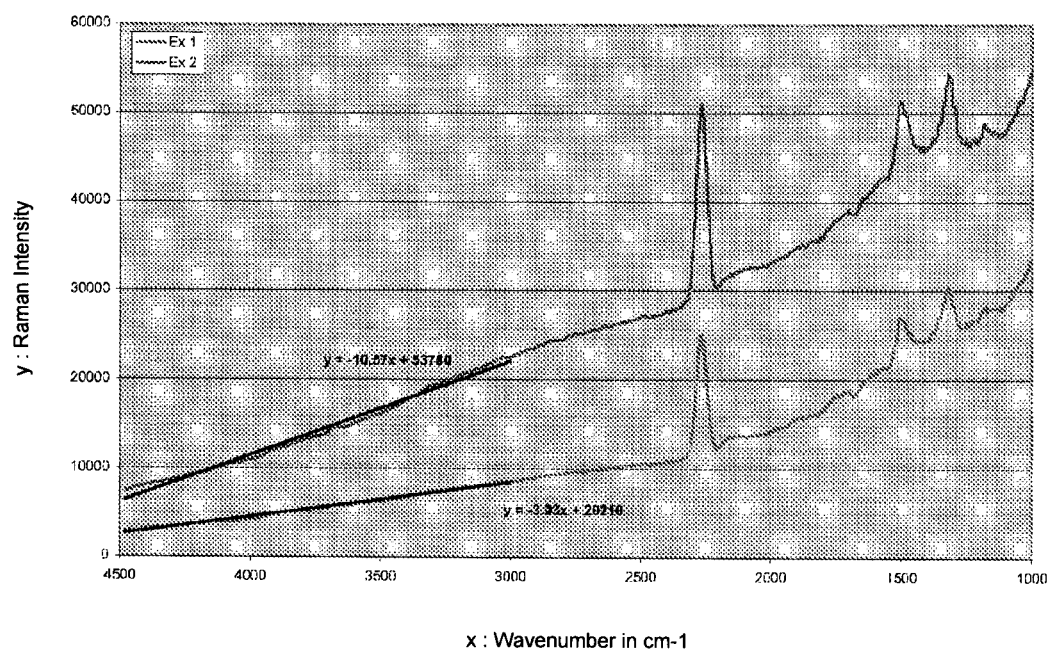

COMPOSITION INCLUDING A PENTACYCLIC ANION SALT AND USE THEREOF AS A BATTERY ELECTROLYTE

FIELD OF THE INVENTION

The present invention relates to the composition of pentacyclic anion salt, and in particular of lithium 1-trifluoromethyl-4,5-dicarbonitrileimidazolate, for battery electrodes.

TECHNICAL BACKGROUND

A lithium-ion battery comprises at least one negative electrode, one positive electrode, a separator and an electrolyte. The electrolyte consists of a lithium salt dissolved in a solvent which is generally a mixture of organic carbonates, in order to have a good compromise between viscosity and dielectric constant.

Among the salts which are the most widely used is lithium hexafluorophosphate ($LiPF_6$), which has many of the numerous qualities required, but has the disadvantage of degrading in the form of hydrofluoric acid gas. This poses safety problems, in particular in the context of the use in the near future of lithium-ion batteries for particular vehicles.

Other salts have therefore been developed for providing electrolytes of Li-ion batteries, and in particular LiTDI (lithium 1-trifluoromethyl-4,5-dicarbonitrileimidazolate) and LiPDI (lithium 1-pentafluoroethyl-4,5-dicarbonitrileimidazolate), as is taught in document WO 2010/023413. These salts have the advantage of having fewer fluorine atoms and of comprising strong carbon-fluorine bonds in place of the weaker phosphorus-fluorine bonds of $LiPF_6$. In addition, these salts have very good conductivities of about 6 mS/cm, and a very good dissociation between the imidazolate anion and the lithium cation.

Document WO 2010/023413 proposes several synthesis routes for the production of these pentacyclic anions, one of which consists of the condensation of diaminomaleonitrile (DAMN) with an acid derivative such as a fluorinated acid anhydride, followed by proton/lithium exchange. The salt obtained is then purified so as to achieve a composition which is optimal with respect to its performance levels within an electrolyte for a Li-ion battery.

However, the salts produced after the purification step of WO 2010/023413 poses a problem in the application for batteries. The common methods of analyses have not made it possible to identify and/or quantify the organic and inorganic impurities, present in the salts, that can be detrimental to their use as an electrolyte in batteries.

A first subject of the present invention is a pentacyclic anion salt composition which does not have the abovementioned drawbacks.

A subject of the present invention is also the use of this composition as an electrolyte in batteries.

A subject of the present invention is also a production process for obtaining the composition according to the first subject.

The invention provides the threshold of content of ionic and nonionic compounds present in the pentacyclic salt composition which is suitable for the performance levels of the electrolyte in a battery, in particular the quality of establishment of the SEI (Solid Electrode Interface) and also the retention of capacity of the battery during charge-discharge cycles.

SUMMARY OF THE INVENTION

The present invention relates to a composition comprising a lithium salt of an imidazole compound of formula (I):

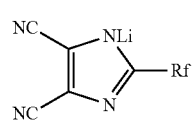

wherein Rf represents a fluorinated alkyl group having from 1 to 5 carbon atom(s), or a fluorine atom.

According to one composition mode, Rf represents $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_6OCF_3$, $C_2F_4OCF_3$, $C_2H_2F_2OCF_3$ or $CF_2OCF_3$, preferably $CF_3$, $C_2F_5$, $C_2F_4OCF_3$, $C_2H_2F_2OCF_3$ or $CF_2OCF_3$.

According to another composition mode, Rf represents F.

The composition, according to the present invention, comprises a salt of formula (I) and at least one cation chosen from the group A made up of sodium, potassium, calcium, iron, magnesium, manganese, strontium, vanadium, ammonium, silver, aluminum, arsenic, barium, silicon, cadmium, cobalt, chromium, copper, nickel, lead, antimony, selenium, tin, strontium and titanium, and at least one anion chosen from the group B made up of fluoride, chloride, nitrate, sulfate, phosphate, acetate, formate, trifluoroacetate, pentafluoroacetate and the anion of formula (II)

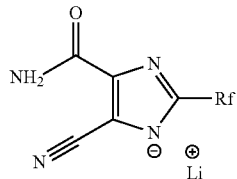

with all of the cation(s) and anion(s) representing at most 1% by weight of the composition.

The present invention makes it possible to overcome the drawbacks of the prior art, in particular by providing optimal electrolytic performance levels at the first charge and the preservation thereof during the charge-discharge cycles. The composition according to the present invention provides a good SEI (Solid Electrode Interface) at the first charge and also an excellent retention of capacity over the course of the working cycles of the battery.

BRIEF DESCRIPTION OF THE DRAWING

FIG. 1 shows RAMAN results with the Y axis showing RAMAN intensity and the X axis showing the wavenumber in $cm^{-1}$.

DETAILED DESCRIPTION OF THE INVENTION

The composition according to the present invention comprises (i) a lithium salt of an imidazole compound of formula (I):

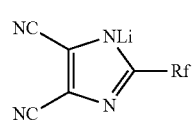

wherein Rf represents a fluorinated alkyl group having from 1 to 5 carbon atom(s), or a fluorine atom, and (ii) at least one cation chosen from the group A made up of sodium, potassium, calcium, iron, magnesium, manganese, strontium, vanadium, ammonium, silver, aluminum, arsenic, barium, silicon, cadmium, cobalt, chromium, copper, nickel, lead, antimony, selenium, tin, strontium and titanium, and (iii) at least one anion chosen from the group B made up of fluoride, chloride, nitrate, sulfate, phosphate, acetate, formate, trifluoroacetate, pentafluoroacetate and the anion of formula (II), with all the cation(s) and anion(s) representing more than 0 and at most 1% by weight of the composition.

According to the embodiments:
the amount of sodium is between 0 and 500 ppm and preferably between 0 and 100 ppm;
the amount of potassium is between 0 and 1000 ppm and preferably between 0 and 500 ppm and advantageously between 0 and 100 ppm;
the amount of calcium is between 0 and 70 ppm;
the amount of iron is between 0 and 10 ppm;
the amount of magnesium is between 0 and 10 ppm;
the amount of manganese is between 0 and 5 ppm;
the amount of strontium is between 0 and 5 ppm;
the amount of vanadium is between 0 and 10 ppm;
the total amount of the following cations: Ag, Al, As, Ba, Si, Cd, Co, Cr, Cu, Ni, Pb, Sb, Se, Sn, Sr, Ti, Zn is between 0 and 200 ppm;
the amount of ammonium ($NH_4^+$) is between 0 and 10 ppm;
the amount of fluoride is between 0 and 100 ppm and preferably between 0 and 10 ppm;
the amount of acetate is between 0 and 30 ppm and preferably between 0 and 5 ppm;
the amount of formate is between 0 and 200 ppm and preferably between 0 and 10 ppm;
the amount of chloride is between 0 and 500 ppm and preferably between 0 and 100 ppm and advantageously between 0 and 50 ppm;
the amount of nitrate is between 0 and 150 ppm and preferably between 0 and 100 ppm and advantageously between 0 and 50 ppm;
the amount of sulfate is between 0 and 500 ppm and preferably between 0 and 150 ppm and advantageously between 0 and 25 ppm;
the amount of phosphate is between 0 and 100 ppm and preferably between 0 and 10 ppm;
the amount of trifluoroacetate is between 0 and 100 ppm;
the amount of pentafluoroacetate is between 0 and 200 ppm and preferably between 0 and 100 ppm;
the amount of the anion of (II) is between 0 and 600 ppm and preferably between 0 and 400 ppm;
Rf represents F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_6OCF_3$, $C_2F_4OCF_3$, $C_2H_2F_2OCF_3$ or $CF_2OCF_3$, preferably $CF_3$, $C_2F_5$, $C_2F_4OCF_3$, $C_2H_2F_2OCF_3$ or $CF_2OCF_3$.

The applicant has discovered that the preferred compositions according to the invention can be characterized by a Raman spectrum baseline which deviates very little relative to the horizontal. The Raman analysis was carried out using a JOBIN YVON microscope under the following conditions:
Green Laser Excitation at 532 nm
Confocal diaphragm=1000 µ
Network 600 lines
Detector 2800 $cm^{-1}$
and the spectra result from the addition of 5 measurements of 16 scans, each of 1 second.

Under these conditions, the deviation of the baseline of the spectrum taken between 4500 $cm^{-1}$ and 3000 $cm^{-1}$ devoid of any Raman line must not exceed a certain slope factor a relative to the horizontal. This factor is defined by linear regression of the baseline of the spectrum between 4500 $cm^{-1}$ and 3000 $cm^{-1}$ with the equation being $y=ax+b$, y being the intensity, x being the wavelength and a representing the slope of this linear regression line relative to the horizontal, and b representing a shift in intensity y at the wavelength 4500 $cm^{-1}$ due to the effect of the fluorescence caused by the traces of impurities. y and b are expressed in constructor Raman intensity units. When the Raman spectrum does not exhibit any baseline deviation due to the presence of fluorescent impurities, $a=0$. The value of b depends on the instrumentation, in particular on the aging state of the laser, and the same powder examined on another Raman microscope would provide a different value of b, and consequently a different Raman intensity y.

On the other hand, the slope a of the regression line for the baseline of the Raman spectrum between 4500 $cm^{-1}$ and 3000 $cm^{-1}$ will remain substantially the same.

The absolute value of the slope a between 4500 $cm^{-1}$ and 3000 $cm^{-1}$ is therefore preferably $a \leq 25$, the maximum permissible slope factor, more preferably $a \leq 15$ and even more preferably $a \leq 5$.

According to one preferred embodiment of the invention, the composition comprises a salt of formula (I) and at least one cation, chosen from the group A, and at least one anion, chosen from the group B, with all the cation(s) and anion(s) representing more than 0 and at most 1% by weight of the composition, and the sodium and/or the potassium (is) are present in an amount greater than 0 ppm and less than or equal to 100 ppm.

According to another preferred mode of the invention, the composition comprises a salt of formula (I) and at least one cation, chosen from the group A, and at least one anion, chosen from the group B, with all the cation(s) and anion(s) representing more than 0 and at most 1% by weight of the composition, and the trifluoroacetate and/or the pentafluoroacetate (is) are present in an amount greater than 0 ppm and less than or equal to 100 ppm.

According to one particularly preferred embodiment of the invention, the composition comprises a salt of formula (I) and at least one cation, chosen from the group A, and at least one anion, chosen from the group B, with all the cation(s) and anion(s) representing more than 0 and at most 1% by weight of the composition, and the sodium and/or the potassium (is) are present in an amount greater than 0 ppm and less than or equal to 100 ppm, and the trifluoroacetate and/or the pentafluoroacetate (is) are present in an amount greater than 0 ppm and less than or equal to 100 ppm.

Whatever the embodiment of the invention, the salt of formula (I) represents at least 99%, preferably at least 99.9% and advantageously at least 99.95% by weight of the composition.

Preferably, the composition comprising the salt of formula (I), when it is present at a concentration of one mol per liter of a solvent, which is nonabsorbent in the visible range, has a Hazen color <10.

As solvent which is nonabsorbent in the visible range, mention may in particular be made of acetonitrile, ethanol, ethyl acetate and water.

Preferably, the compound of formula (I) is lithium 1-trifluoromethyl-4,5-dicarbonitrileimidazolate.

When the compound of formula (I) is lithium 1-trifluoromethyl-4,5-dicarbonitrileimidazolate, the lithium represents between 3.4% and 3.8% by weight, preferably between 3.55% and 3.65% by weight and advantageously between 3.59 and 3.61% by weight of the composition according to the invention.

Preparation of Lithium Imidazolate

A subject of the present invention is also a process for obtaining the composition according to the first subject. This process comprises at least one step of treating a solution of salt containing the compound of formula (I), which has been previously prepared, on activated carbon, followed by at least one step of recrystallization of the treated solution.

The solution of salt containing the compound of formula (I) can be prepared according to the method described in document WO 2010/023413 (page 10 line 28 to page 12 line 16), namely preparation, in a first step, of an acid starting from diaminomaleonitrile by condensation with anhydride or aldehyde O=CHR$_f$ or ketal, followed by a second step during which the acid is converted into lithium salt. This solution can also be prepared according to the method described in document WO 2013/072591.

The process for preparing a composition of salt of formula (I) as described above comprises (i) at least one step of treating a solution resulting from the reaction of an imidazole compound of formula (III), in the presence of a solvent (S), with a lithium base, preferably chosen from lithium hydride, lithium carbonate, lithium hydroxide and combinations thereof, on activated carbon; (ii) at least one step of separating the activated carbon so as to give a solution of composition of salt of formula (I) in the solvent (S), and (iii) at least one step of concentrating the solution obtained in step (ii), followed by at least one step of cooling until the formation of crystals and (iv) at least one filter-drying and/or filtering step, followed by at least one drying step.

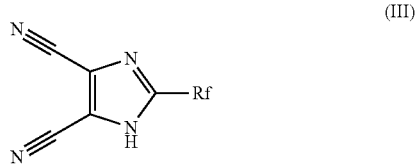

(III)

Preferably, the cooling step is carried out when the solution is concentrated by a volume factor of between 50 and 2, preferably between 20 and 2 and more preferably between 15 and 2.

According to one variant of the process, the solution recovered in step (ii) is evaporated to dryness, then the solid obtained is dissolved in a solvent (S), different than the one used for step (i), before the crystallization step (iii) described above.

The cooling temperature may be between −150 and 0° C., preferably between −12 and −2° C.

The typical recrystallization yield for LiTDi under these conditions is about 90%.

For example, LiTDI is obtained when Rf represents a trifluoromethyl group, and LiPDI when Rf represents a pentafluoroethyl group.

As solvent (S), mention may in particular be made of water, or an organic solvent, preferably chosen from acetonitrile, alcohols such as methanol, ethanol, isopropanol, n-butanol or benzyl alcohol, ethyl acetate, alkyl carbonates such as ethylene or dimethyl carbonates, and tetrahydrofuran (THF).

Preferably, an organic solvent is used for the reaction step for lithiation of an imidazole compound of formula (III) and/or the step of treating with activated carbon. The solvent for the lithiation reaction may be different than the one for the step of treating with activated carbon.

Advantageously, the process is carried out in the presence of acetonitrile for the step (i) of treating with activated carbon and/or for the redissolving after the step of evaporating to dryness.

The activated carbon is preferably chosen from commercially available grades of carbons termed physical carbons, i.e. activated only with steam at high temperature. Among the physical carbons, those derived from "soft" vegetable raw material, such as pine, are particularly preferred.

The activated carbon may be powdered or in the form of grains, or in the form of composite filtering media obtained by mixing the powdered carbon with a binder that is inert with respect to the abovementioned organic solvents or to water. The activated carbon in the form of grains or of filters is, however, preferred in order to limit the dust during processing.

The porosity of the activated carbon, measured by $N_2$-BET, is preferably between 900 and 1800 m$^2$/g, advantageously between 900 and 1300 m$^2$/g and more particularly between 900 and 1100 m$^2$/g.

The main porosity of the activated carbon may be microporous, mesoporous or macroporous in nature. Mesoporosity is preferred. The particle size D10 of the activated carbon used for the treatment is preferably between 5 and 10 μm, advantageously between 5 and 8 μm.

The particle size D50 of the activated carbon used for the treatment is preferably between 20 and 40 μm, advantageously between 25 and 35 μm. A particle size D50 of between 28 and 30 μm is particularly preferred.

The ash content is preferably less than or equal to 5% by weight, advantageously less than or equal to 3% by weight for the steam-activated carbons.

For the physical carbons washed with acid, the ash content is preferably less than 1% by weight.

The initial pH of the carbon, measured on the filtrate obtained after dissolving 4 g in 100 ml of water decarbonated by boiling, followed by boiling for 10 min and then filtration under hot conditions, is preferably between 10 and 6 and advantageously between 10 and 7.

Preferably, the solution of the composition of salt of formula (I) used for the step of treating with activated carbon is between 50 and 500 g of salt per liter of solvent, advantageously between 100 and 250 g/l. A solution of between 130 and 200 g of LiTDI per liter of acetonitrile has given particularly advantageous results.

Preferably, the weight ratio of the carbon used/weight of (I) in the solution to be treated is between 1:5 and 1:8. The solutions in acetonitrile, the preferred solvent according to the invention, are established with a carbon versus (I) weight ratio of between 1:5 and 1:8, and preferably between 1:6 and 1:8. Thus, treatment with 1 g of carbon for 7.5 g of LiTDI solid salt has given advantageous results.

The temperature for treatment with activated carbon is preferably between 0 and 60° C.

The powdered activated carbons of the CECA 2SW and 3SW range or any filtering media based on these grades are particularly suitable.

According to one embodiment, the activated carbon is subjected to aqueous leaching before use in step (i). The aqueous leaching can be carried out with distilled or deionized water and powdered activated carbon by means of a filter using a pressure ranging up to 3 bar.

By way of example, the applicant has obtained for a molar solution of salt (I) in an organic solvent, a Hazen color <10 after several steps of treating, with activated carbon, a brown-colored initial solution, typically with an absorption of 5 to 7 according to the Gardner standard.

At the end of the treatment with activated carbon, the salt of formula (I) is subjected to a step of recrystallization from an organic solvent.

Preparation of an Electrolyte

The compounds of formula (I) thus prepared, in particular LiTDI and LiPDI, can be used for the preparation of an electrolyte, by solubilizing them in an appropriate solvent.

The compounds of formula (I) are, for example, dissolved in a solvent or a mixture of solvents of from 1 to 5 constituent(s) chosen from the following carbonates: ethylene carbonate, dimethyl carbonate, ethylmethyl carbonate, diethylcarbonate, propylene carbonate and the following glymes: ethylene glycol dimethyl ether, diethylene glycol dimethyl ether, dipropylene glycol dimethyl ether, diethylene glycol diethyl ether, triethylene glycol dimethyl ether, diethylene glycol dibutyl ether, tetraethylene glycol dimethyl ether and diethylene glycol t-butyl methyl ether. When a solvent mixture is used, the weight proportions of each of the constituents are preferably between 1 and 10 relative to the constituent that is present in the smallest amount, more preferentially between 1 and 8.

The concentration of compound of formula (I) in the electrolyte is preferably from 0.1 mol/l to 5 mol/l and advantageously from 0.2 mol/l to 2.5 mol/l.

This electrolyte can then be used for the manufacture of batteries or battery cells, by placing it between a cathode and an anode, in a manner known per se.

EXPERIMENTAL SECTION

The Hazen color is measured according to the Hazen standard, for a dissolution of (I) in a solvent which is nonabsorbent in the visible range, at a concentration of 1 mol/l, on a Hach Lico150 spectrophotometer, in a cell 11 mm in diameter. When a solution gives a value below 10 Hazen, the optical path is increased by using a 50 mm cuvette for greater accuracy. The Hazen values given in the examples are the means of 3 measurements of the same solution.

The ICP-AES data are obtained on an ICAP 6500 spectrometer (Thermo Electronics).

Sampling for the quantification of Li, K, Na and traces of elements of the list provided:

The sample of (I) is dissolved in ultrapure water. 2 dilutions were used: 1 g/l for the determination of Na, K, and elements Ag, Al, As, Ba, Si, Cd, Co, Cr, Cu, Ni, Pb, Sb, Se, Sn, Sr, Ti, Zn in trace amounts, and 0.1 g/l for the analysis of lithium.

Qualitative panoramic analysis:

The ICP-AES conditions applied for the semi-quantitative "panoramic" analysis of the elements and trace amounts are:
Plasma source output power: 1150 W
Nebulizer gas flow rate: 0.7 l/min
Cooling flow rate=16 l/min
Torch height: 12 mm
Pump speed: 50 rpm
Spectral bandwidth: 7 pm to 200 nm, 3.5 nm per pixel
Wavelength range: 167 nm to 847 nm.

The ICP-AES quantification method for measuring Li, K and Na used 5 calibration points.

For the analysis of the elements in trace amounts Ag, Al, As, Ba, Si, Cd, Co, Cr, Cu, Ni, Pb, Sb, Se, Sn, Sr, Ti and Zn, the semi-quantitative method is based on two calibration points.

For the two methods, the calibration is carried out by adding standards to the sample itself so as to minimize the matrix effects.

ICP-AES is preferred to cationic chromatography in aqueous solution for measuring the elements Li, Na and K.

For the examples, the conditions for anion analysis in ion chromatography (IC) are the following:
Apparatus Dionex ICS 5000 DUAL
Column ASII-HC
Flow rate 1 ml/min
Eluent KOH in a gradient of from 2 mmol/l to 20 mmol/l in the course of 15 minutes
Conductimetric detection
Suppressor ASRS 4 mm with 50 mA of applied current.
Injection of 50 µl of solutions of LiTDI 5 g/l and 10 g/l according to required sensitivity per anionic species present.
Calibration of each anionic species with five synthetic solutions ranging from 0.05 mg/l up to 1 mg/l.

For the examples, the conditions for NMR analysis of the fluorinated species such as (I) or (II) in $^{19}F$, $^{1}H$ and $^{13}C$ NMR are the following:

Equipment:

The NMR spectra and quantifications were carried out on a Bruker AV 400 spectrometer, at 100.62 MHz for $^{13}C$ and 376.47 MHz for $^{19}F$, on a 5 mm probe of $BBFO^{+}$ type.

Sampling:

The samples of (I) are dissolved in DMSO-d6 (approximately 30 mg in 0.6 ml). In the case of the detection of fluorides or additional LiF used to verify the unwanted presence of fluorides, the solvent of (I) is $D_2O$ because of the insolubility of LiF in DMSO.

Quantification:

The relative quantification by 19F NMR is carried out by integration of the signals of the fluorinated species, weighted by the number of fluorines contributing to the signal, a method well known to those skilled in the art.

The absolute quantification by $^{19}F$ NMR is carried out by metered addition of α,α,α-trifluorotoluene (TFT), Aldrich, to the tube containing (I), and by integration of the signals of the fluorinated species to be assayed in comparison with that of the $CF_3$ groups of this internal standard, according to a method well known to those skilled in the art. The limit of quantification of a species such as (II) at the frequency of 376.47 MHz and with the probe chosen is about fifty ppm or so.

The mass spectrometry makes it possible to confirm the empirical formula of the organic impurities of (I), such as (II), under the following experimental conditions:

Equipment:

The mass spectrometry spectra are recorded on a WATERS QTOF II spectrometer, using positive and negative ionization of the molecules of (I) or of the organic impurities such as (II).

Sampling:

The samples of (I) with $Rf=CF_3$ (LiTDI) are dissolved in methanol at the concentration of 100 mg/l. They are directly injected into the mass spectrometer using the flow injection mode in a 70/30 by volume methanol/water mixture.

Experimental Conditions:

| Electrospary positive mode<br>Positive electrospray ion source | Electrospray negative mode<br>negative electrospray ion source |
|---|---|
| Capillary: 3 kV | Capillary: 3 KV |
| Cone: 30 V | Cone: 30 V |
| Extractor: 0 V | Extractor: 2 V |

| Electrospary positive mode Positive electrospray ion source | Electrospray negative mode negative electrospray ion source |
|---|---|
| Source temperature: 80° C. dessolvation temperature: 150° C. | Source temperature: 80° C. dessolvation temperature: 150° C. |
| Quadrupole analyser | |
| Collision energy: 10 eV Steering: 1.00 V Entrance: 65 eV Pre-filter: 6 V | Collision energy: 10 eV Steering: 1.00 V Entrance: 65 eV Pre-filter: 6 V |
| TOF analyser | |
| Transport: 3.0 V Accelerator voltage: 200 V Focus: 0 V Tube lens: 90 V Pusher: 980 V TOF: 9.1 kV Reflectron: 36.00 Pusher cycle time (μs): auto Multiplier: 550 MCP: 2100 V | Transport: 5.0 V Accelerator voltage: 200 V Focus: 0.3 V Tube lens: 100 V Pusher: 980 V TOF: 9.1 kV Reflectron: 36.00 Pusher cycle time (μs): 42 μs Multiplier: 550 MCP: 2100 V |

EXAMPLE 1

In a 4-liter jacketed stirred reactor equipped with a condenser, with a dropping funnel and with a thermocouple, 867.35 g of 98%-pure DAMN are placed in 2979.29 g of 1,4-dioxane at ambient temperature. The suspension is stirred while 1751.57 g of 99%-pure trifluoroacetic anhydride are introduced dropwise by means of the dropping funnel, while maintaining the reaction medium at a temperature below 30° C. The suspension rapidly changes into a brown-colored solution. When all of the trifluoroacetic anhydride has been introduced, the temperature of the reaction medium is increased to the reflux of dioxane (105° C.). After 30 minutes of reflux, the temperature is decreased to 50° C. The content of the reactor is then evaporated using a rotary evaporator under a high vacuum (<10 mmHg) until a brown oil is obtained. This oil is then taken up with water in a 5-liter beaker, with a water:oil ratio of 1:1. The whole mixture is stirred and heated at 60° C. until a homogeneous brown paste is obtained, then rapidly cooled in a bath of cold water and ice. The crystals obtained are then filtered off and rinsed with 500 ml of toluene and then filtered-dried under vacuum.

The crystals thus filter-dried are redissolved in water with a crystal/water weight ratio of 1:1, at a temperature of 60° C., and then rapidly cooled. The crystals obtained are filtered off, rinsed and filter-dried as previously.

After a further recrystallization operation, the crystals are analyzed by $^{19}F$ NMR and show a relative fluorinated-species composition of 99.7% of HTDI, 0.2% of amide of HTDI having a structure identified by NMR and mass spectrometry as being the compound of formula (III) and 900 ppm of trifluoroacetic acid (TFA).

The crystals previously obtained are dissolved, at a temperature of approximately 40° C., in acetonitrile in a proportion of 1 g of crystals for 3.5 ml of solvent. $Li_2CO_3$ in solid form is then added thereto in small amounts, up to 290.2 g, and the mixture is left to stir at ambient temperature overnight. Acetonitrile is then added thereto so as to obtain a concentration of 1 g of salt for approximately 7.2 ml of solvent.

The resulting solution is then treated with CECA 3SW powdered activated carbon, washed beforehand with deionized water, in a proportion of 1 g of carbon for 7.5 g of LiTDI salt, for 3 hours at ambient temperature. At the end of the treatment, the solution is filtered.

The treatment is carried out again with a new feedstock of activated carbon.

After 4 treatments, a solution having a color of 6 Hazen is obtained.

After evaporation of the acetonitrile and drying at 120° C. under vacuum for 1 week, 1118 g of solid are obtained.

The $^{19}F$ NMR analysis with internal calibration with α,α,α-trifluorotoluene gives a composition comprising 99.74% by weight of LiTDI, 0.19% of amide of LiTDI and 730 ppm of lithium trifluoroacetate (Li-TFA). 230 g of the solid are sampled so as to dissolve it in 900 ml of acetonitrile at 65° C. in a 2-liter round-bottomed flask equipped with a condenser and with a magnetic bar. After the solid has completely dissolved, the round-bottomed flask is placed in an ice/salt bath which brings the LiTDI solution to −2° C., after having stopped for stirring. The ice bath is left to warm up naturally, the residence time in the cold bath being at least 5 hours, then the round-bottomed flask containing crystalline LiTDI and acetonitrile having a very slightly yellowish color is transferred for evaporation under a moderate vacuum into a heating bath at 40° C. so as to concentrate the volume of acetonitrile by a factor of 3.

The whole mixture is then filtered at ambient temperature and the white LiTDI crystals represent a weight of 210 g, i.e. an acetonitrile recrystallization yield of 91.3%. This fraction thus recrystallized has a purity determined by $^{19}F$ NMR and internal calibration with α,α,α-trifluorotoluene >99.95% by weight of LiTDI and exhibits about 200 ppm of Li-amide and less than 100 ppm of Li-TFA.

The ICP analysis of the solid obtained, the color and the performance levels in a battery are summarized in the table hereinafter.

| Element or impurity (determination method) | Abundance in ppm | Hazen value | SEI: Irreversible capacity | Capacity retention |
|---|---|---|---|---|
| Li (ICP-AES) | 3.5% | 6 | 14% | 20% after 720 cycles carried out at a regime of 1C |
| Na (ICP-AES) | 30 | | (EC/EMC | |
| K (ICP-AES) | ND | | 3/7 v/v) | |
| Ca (ICP-AES) | <10 | | | |
| Fe (ICP-AES) | <5 | | | |
| Sr (ICP-AES) | <5 | | | |
| V (ICP-AES) | <5 | | | |
| $NH_4^+$ ($^1H$ NMR) | ND | | | |
| F— (IC) | 8 | | | |
| $CH_3COO$— (IC) | 30 | | | |
| HCOO— (IC) | 9 | | | |
| Cl— (IC) | 3 | | | |
| TFA— (IC) | 71 | | | |
| $NO_3^-$ (IC) | 2 | | | |
| $SO_4^{2-}$ (IC) | 31 | | | |

Composition of the solid as relative % by weight according to $^{19}F$ NMR analysis:

| Fluorinated species | Relative amount of the fluorinated species |
|---|---|
| (I) | 99.97% |
| (III) | 222 ppm |
| TFA— | 98 ppm |

Composition of the solid as absolute % by weight according to $^{19}F$ NMR analysis, by internal calibration with α,α,α-trifluorotoluene (TFT) from Aldrich:

| Fluorinated species | Absolute amount of the fluorinated species |
|---|---|
| (I) | >99.95% |
| (III) | 210 ± 30 ppm* |
| TFA— | 93 ± 10 ppm* |

*mean of 2 calibrations

RAMAN result: the slope, in absolute value, of y=ax+b is a=3.93.

EXAMPLE 2

The process is carried out as previously, but on a pilot for a targeted amount of LiTDI of 35 kg. A 100-liter reactor is used in place of the 4-liter stirred reactor and a 400-liter reactor is used for the treatments with activated carbon under dilute conditions. The conditioning of the activated carbons by washing with water and also the filtrations thereof were carried out in a Tournaire filter fitted with a PP cloth of 11 μm.

The ICP analysis of the solid obtained, the color and the performance levels in a battery are summarized in the table hereinafter:

| Element or impurity | Abundance in ppm | Hazen value | SEI: Irreversible capacity | Capacity retention |
|---|---|---|---|---|
| Li (ICP-AES) | 3.6% | 7 | 16% (EC/EMC 1/1 v/v) | 21% after 820 cycles in regime 1C |
| Na (ICP-AES) | 20 ppm | | | |
| K (ICP-AES) | <LOD of 10 ppm, | | | |
| Ca | <LOD of 9.4 ppm | | | |
| Fe | <LOD 0.5 ppm | | | |
| Sr | <LOD of 0.01 ppm | | | |
| V | <LOD of 1.2 ppm | | | |
| $NH_4^+$ | ND ($^1$H NMR) | | | |
| F— (IC) | ND | | | |
| $CH_3COO$— (IC) | ND | | | |
| HCOO— (IC) | ND | | | |
| Cl— (IC) | ND | | | |
| TFA— | 40 ppm | | | |
| $NO_3^-$ | 1 ppm | | | |
| $SO_4^{2-}$ | 12 ppm | | | |
| $PO_4^{3-}$ | 7 ppm | | | |

Set of ICP-AES measurements of the cations

| | Result (ppm) | LOD |
|---|---|---|
| LOD = Limit of detection, in ppmAg | <LOD | 0.9 |
| Al | <LOD | 0.6 |
| As | <LOD | 2.2 |
| B | <LOD | 0.3 |
| Ba | <LOD | 0.1 |
| Ca | <LOD | 9.4 |
| Cd | <LOD | 0.6 |
| Co | <LOD | 0.8 |
| Cr | <LOD | 1.0 |
| Cu | <LOD | 0.7 |
| Fe | <LOD | 0.5 |
| Mg | <LOD | 0.4 |
| Mn | <LOD | 0.1 |
| Mo | <LOD | 0.5 |
| P | 2.40 | 2.2 |
| Sb | <LOD | 2.2 |
| Si | <LOD | 1.9 |
| Sn | <LOD | 1.8 |
| Sr | <LOD | 0.01 |
| Ti | <LOD | 0.2 |
| V | <LOD | 1.2 |
| Zn | <LOD | 0.2 |

Composition of solid as relative % by weight according to $^{19}$F NMR analysis:

| Fluorinated species | Relative amount of the fluorinated species |
|---|---|
| (I) | 99.96% |
| (III) | 315 ppm |
| TFA— | 42 ppm |

RAMAN result: the slope in absolute value of the linear regression straight line y=ax+b for the baseline of the spectrum between $x=4500$ $cm^{-1}$ and $x=3000$ $cm^{-1}$ is a=10.57

FIG. 1 gives the 532 nm Raman spectra of examples 1 and 2. The linear regression of the baseline ranging from 4500 $cm^{-1}$ to 3000 $cm^{-1}$ gives a straight line having the equation y=ax+b, with y the Raman intensity, a the slope of the straight line relative to the horizontal, x the Raman wavenumber, and b the shift in the straight line at the wavenumber x=0 relative to the intensity y=0.

The invention claimed is:

1. A composition comprising (i) a lithium salt of an imidazole compound of formula (I):

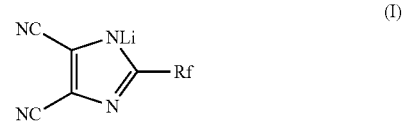

(I)

wherein Rf represents a fluorinated alkyl group having from 1 to 5 carbon atom(s), or a fluorine atom, and (ii) at least one cation chosen from the group A made up of sodium, potassium, calcium, iron, magnesium, manganese, strontium, vanadium, ammonium, silver, aluminum, arsenic, barium, silicon, cadmium, cobalt, chromium, copper, nickel, lead, antimony, selenium, tin, strontium and titanium, and (iii) at least one anion chosen from the group B made up of fluoride, chloride, nitrate, sulfate, phosphate, acetate, formate, trifluoroacetate, pentafluoroacetate and the anion of formula (II)

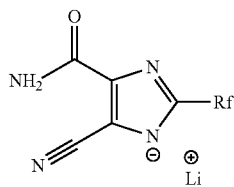

with all of the cation(s) and anion(s) representing more than 0 and at most 1% by weight of the composition.

2. The composition as claimed in claim 1, comprising at least one of the following characteristics:
the amount of sodium is between 0 and 500 ppm;
the amount of potassium is between 0 and 1000 ppm;
the amount of calcium is between 0 and 70 ppm;
the amount of iron is between 0 and 10 ppm;
the amount of magnesium is between 0 and 10 ppm;
the amount of manganese is between 0 and 5 ppm;
the amount of strontium is between 0 and 5 ppm;
the amount of vanadium is between 0 and 10 ppm;
the total amount of the following cations: Ag, Al, As, Ba, Si, Cd, Co, Cr, Cu, Ni, Pb, Sb, Se, Sn, Sr, Ti, Zn is between 0 and 200 ppm;
the amount of ammonium ($NH_4^+$) is between 0 and 10 ppm;
the amount of fluoride is between 0 and 100 ppm;
the amount of acetate is between 0 and 30 ppm;
the amount of formate is between 0 and 200 ppm;
the amount of chloride is between 0 and 500 ppm;
the amount of nitrate is between 0 and 150 ppm;
the amount of sulfate is between 0 and 500 ppm;
the amount of phosphate is between 0 and 100 ppm;
the amount of trifluoroacetate is between 0 and 100 ppm;
the amount of pentafluoroacetate is between 0 and 200 ppm;
the amount of the anion of (II) is between 0 and 600 ppm;
Rf represents F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_6OCF_3$, $C_2F_4OCF_3$, $C_2H_2F_2OCF_3$ or $CF_2OCF_3$.

3. The composition as claimed in claim 1, wherein the absolute value of slope a, relative to the horizontal, of the baseline of the Raman spectrum, taken between 4500 cm$^{-1}$ and 3000 cm$^{-1}$, for a linear regression straight line having the equation y=ax+b is ≤25.

4. The composition as claimed in claim 1, wherein the sodium and/or the potassium (is) are present in an amount greater than 0 ppm and less than or equal to 100 ppm.

5. The composition as claimed claim 1, wherein the trifluoroacetate and/or the pentafluoroacetate (is) are present in an amount greater than 0 ppm and less than or equal to 100 ppm.

6. The composition as claimed in claim 1, wherein the salt of formula (I) represents at least 99% by weight of the composition.

7. The composition as claimed in claim 1, wherein it has a Hazen color <10 for a concentration of one mol for the salt of formula (I) per liter of a solvent, which is nonabsorbent in the visible range.

8. The composition as claimed in claim 1, wherein the compound of formula (I) is lithium 1-trifluoromethyl-4,5-dicarbonitrileimidazolate.

9. A process for preparing the composition as claimed in claim 1, wherein it comprises at least one step of treating a solution of salt containing the compound of formula (I), which has been previously prepared from diaminomaleonitrile, on activated carbon, followed by at least one step of recrystallization of the treated solution.

10. The process as claimed in claim 9, wherein it comprises (i) at least one step of treating a solution resulting from the reaction of an imidazole compound of formula (III),

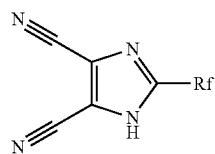

in the presence of a solvent (S), with a lithium base; (ii) at least one step of separating the activated carbon so as to give a solution of composition of salt of formula (I) in the solvent (S); and (iii) at least one step of concentrating the solution obtained in step (ii), followed by at least one step of cooling until the formation of crystals and (iv) at least one filter-drying and/or filtering step, followed by at least one drying step.

11. The process as claimed in claim 10, wherein solution recovered in step (ii) is evaporated to dryness, then the solid obtained is dissolved in a solvent (S), different than the one used for step (i), before the crystallization step (iii) described above.

12. The process as claimed in claim 10, wherein the solvent (S) is chosen from water or an organic solvent.

13. The process as claimed in claim 9, wherein the activated carbon is chosen from the commercially available grades of carbons termed physical carbons.

14. The process as claimed in claim 9, wherein the activated carbon is powdered or in the form of grains, or in the form of composite filtering media.

15. The process as claimed in claim 9, wherein the porosity of the activated carbon, measured by $N_2$-BET, is between 900 and 1800 m$^2$/g.

16. The use of the composition as claimed in claim 1 as an electrolyte.

* * * * *